(12) United States Patent
Rahma et al.

(10) Patent No.: US 12,332,209 B2
(45) Date of Patent: Jun. 17, 2025

(54) ELECTROLYTE ANALYSIS DEVICE

(71) Applicant: Hitachi High-Tech Corporation, Tokyo (JP)

(72) Inventors: Hutami Rahayu Rahma, Tokyo (JP); Masafumi Miyake, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 391 days.

(21) Appl. No.: 17/795,610

(22) PCT Filed: Jan. 13, 2021

(86) PCT No.: PCT/JP2021/000764
§ 371 (c)(1),
(2) Date: Jul. 27, 2022

(87) PCT Pub. No.: WO2021/161704
PCT Pub. Date: Aug. 19, 2021

(65) Prior Publication Data
US 2023/0075119 A1 Mar. 9, 2023

(30) Foreign Application Priority Data
Feb. 14, 2020 (JP) .................. 2020-023832

(51) Int. Cl.
*G01N 27/333* (2006.01)
*G01N 27/30* (2006.01)
(Continued)

(52) U.S. Cl.
CPC ......... *G01N 27/333* (2013.01); *G01N 27/301* (2013.01); *G01N 27/4166* (2013.01); *G01N 33/18* (2013.01)

(58) Field of Classification Search
CPC ............... G01N 27/333; G01N 27/301; G01N 27/4166; G01N 33/18
See application file for complete search history.

(56) References Cited

U.S. PATENT DOCUMENTS

2009/0087914 A1  4/2009  Kuroda
2009/0114538 A1  5/2009  Takayama et al.
(Continued)

FOREIGN PATENT DOCUMENTS

JP   4-291147 A   10/1992
JP   8-211016 A    8/1996
(Continued)

OTHER PUBLICATIONS

Lladosa et al., Effect of the reference solution in the measurement of ion activity coefficients using cells with transference at T=298.15 K, J. Chem. Thermodynamics, 2010, 42, pp. 244-250 (Year: 2010).*
(Continued)

*Primary Examiner* — Luan V Van
*Assistant Examiner* — Randall Lee Gamble, Jr.
(74) *Attorney, Agent, or Firm* — Crowell & Moring LLP (57) ABSTRACT

Provided is an electrolyte analysis device capable of suppressing a burden with respect to measurement while suppressing a decrease in accuracy of a measurement result. An electrolyte analysis device 100 that measures a concentration of a specific ion in a sample using a plurality of ion selective electrodes of an ion selective electrode group 102, and a reference electrode 103 includes a water supply tank 107 configured to store system water used for at least one of solution sending, probe cleaning, and temperature adjustment in the electrolyte analysis device 100, a specimen dispensing device 101 configured to dispense a sample to be measured, a dilution tank 106 configured to dilute the sample dispensed by the specimen dispensing device 101 with the system water, a water quality measurement unit 200 configured to measure the ion concentration of the system water in the water supply tank 107, and a control device 111 configured to control the electrolyte analysis device 100, in which the control device 111 performs water quality deter- (Continued)

mination processing of determining whether a water quality of the system water is normal or abnormal based on a measurement result of the water quality measurement unit 200.

8 Claims, 5 Drawing Sheets

(51) Int. Cl.
*G01N 27/416* (2006.01)
*G01N 33/18* (2006.01)

(56) References Cited

U.S. PATENT DOCUMENTS

| | | | | |
|---|---|---|---|---|
| 2011/0213229 | A1* | 9/2011 | Benoit | G01N 33/726 252/502 |
| 2012/0261260 | A1 | 10/2012 | Li et al. | |
| 2016/0341692 | A1* | 11/2016 | Tonomura | G01N 27/283 |
| 2018/0238829 | A1* | 8/2018 | Watanabe | G01N 27/4166 |
| 2019/0265187 | A1 | 8/2019 | Kishioka et al. | |

FOREIGN PATENT DOCUMENTS

| | | | | |
|---|---|---|---|---|
| JP | 2001-264283 | A | | 9/2001 |
| JP | 2007-285708 | A | | 11/2007 |
| JP | 2009-133851 | A | | 6/2009 |
| JP | 2011-122823 | A | | 6/2011 |
| JP | 2012058117 | A | * | 3/2012 |
| JP | 2016-218067 | A | | 12/2016 |
| JP | 2018-17543 | A | | 2/2018 |
| JP | 2018017543 | A | * | 2/2018 ............... G01N 1/00 |

OTHER PUBLICATIONS

Kishioka and Ono, English translation of JP 2018-017543A, 2018 (Year: 2018).*
Machine Translation of Akiyama (JP2012058117A) (Year: 2012).*
International Search Report (PCT/ISA/210) issued in PCT Application No. PCT/JP2021/000764 dated Mar. 30, 2021 with English translation (five (5) pages).
Japanese-language Written Opinion (PCT/ISA/237) issued in PCT Application No. PCT/JP2021/000764 dated Mar. 30, 2021 (four (4) pages).

* cited by examiner

ELECTROLYTE ANALYSIS DEVICE

TECHNICAL FIELD

The present invention relates to an electrolyte analysis device.

BACKGROUND ART

An electrolyte analysis device is a device that measures a concentration of a specific electrolyte contained in an electrolyte solution (hereinafter, may be referred to as a specimen) such as blood or urine of a human body, and examples thereof include an electrolyte analysis device using an ion selective electrode method in which concentration measurement is performed using an ion selective electrode (ISE). As the electrolyte analysis device, for example, a flow-type electrolyte analysis device is known. In the flow-type electrolyte analysis device, as an electrolyte solution, a sample solution obtained by diluting serum directly or with a specimen diluent is supplied to the ion selective electrode, and an inter-solution potential between the ion selective electrode and a reference electrode solution is measured. Subsequently (or before measurement), a standard solution having a known electrolyte concentration is supplied to the ion selective electrode, and an inter-solution potential between the standard solution and the reference electrode solution is measured in the same manner as the serum (or the sample solution). Then, an electrolyte concentration of the serum (or the sample solution) can be calculated based on two inter-solution potentials including the inter-solution potential of the standard solution and the inter-solution potential of the serum (or the sample solution).

As a measurement method using such an electrolyte analysis device, for example, PTL 1 discloses a method for measuring a chlorine ion concentration in which a chlorine ion selective electrode and a reference electrode are immersed in a solution to be measured, and when a chlorine ion concentration in the solution to be measured is measured by a potential difference between the two electrodes, a silver/silver chloride electrode is used as the chlorine ion selective electrode, and silver chloride is dissolved at a saturated concentration in a solution in contact with the electrode.

In addition, PTL 2 discloses an electrolyte concentration measurement device including: a measurement unit that includes an ion selective electrode, a reference electrode, and a potential measurement unit, and that measures, by the potential measurement unit, a potential difference when an internal standard solution or a specimen is supplied to the ion selective electrode; a reagent supply unit that supplies a reagent containing the internal standard solution to the measurement unit; a recording and calculating unit that processes information on the potential difference measured by the measurement unit to calculate an ion concentration in the internal standard solution or the specimen; a concentration value correction and determination unit that determines whether the ion concentration in the internal standard solution calculated by the recording and calculating unit is within a range of a preset value and that corrects the ion concentration value in the internal standard solution calculated by the recording and calculating unit; an output unit that outputs a result determined by the concentration value correction and determination unit; and a control unit that controls the measurement unit, the recording and calculating unit, the concentration value correction and determination unit, and the output unit. The reagent supply unit includes: a bottle storage unit that stores, for each type of the reagent, a plurality of bottles each storing a reagent such as the internal standard solution; and a bottle switching unit that detects a remaining amount of the reagent in each of the plurality of bottles stored in the bottle storage unit and supplies the reagent to the measurement unit, thereby switching a bottle in which the remaining amount of the reagent is smaller than a preset amount to a bottle, among bottles stored in the bottle storage unit in which the same type of reagent is contained, in which the remaining amount of the reagent is sufficiently larger than the preset amount, and supplying the reagent to the measurement unit. When, among the plurality of bottles containing the same type of reagent, a bottle for supplying the reagent to the measurement unit is switched by the reagent supply unit, the concentration value correction and determination unit corrects the ion concentration in the internal standard solution or the specimen calculated by the recording and calculating unit after the bottle containing the same type of reagent is switched using information on the ion concentration in the internal standard solution or the specimen calculated by the recording and calculating unit before the bottle is switched.

CITATION LIST

Patent Literature

PTL 1: JP-A-H08-211016
PTL 2: JP-A-2018-17543

SUMMARY OF INVENTION

Technical Problem

In the related art described in PTL 1, a silver nitrate solution (AgNO3) is used as a diluent. However, when a silver nitrate solution is used as the diluent, a wastewater treatment is indispensable in consideration of environmental load, and the wastewater treatment causes an increase in treatment cost and treatment time. In particular, in large-scale hospitals or clinical test centers that perform a large number of measurement treatments, a usage of the diluent and the amount of wastewater are large. Therefore, a burden such as running cost is enormous.

In the related art described in PTL 2, a diluent is generated by mixing a stock solution of the diluent with pure water. However, even in this case, the wastewater treatment is indispensable in consideration of the environmental load, and the burden is large. In addition, since in a clinical test field, pure water is not standardized, there is a possibility that an error occurs in a measurement result of the electrolyte analysis device due to an unspecified ion contained in the pure water.

The invention is made in view of the above problems, and an object of the invention is to provide an electrolyte analysis device capable of suppressing a burden with respect to measurement while suppressing s a decrease in accuracy of a measurement result.

Solution to Problem

The present application includes a plurality of solutions for solving the above problems, and an example thereof is an electrolyte analysis device that measures a concentration of a specific ion in a sample using a plurality of ion selective electrodes and a reference electrode. The electrolyte analysis device includes: a water supply tank configured to store a diluent used for at least one of solution sending, probe cleaning, and temperature adjustment in the electrolyte analysis device; a specimen dispensing device configured to dispense a sample to be measured; a dilution tank configured to dilute the sample dispensed by the specimen dispensing device with the diluent; a water quality measurement unit configured to measure an ion concentration of the diluent in the water supply tank; and a control device configured to control the electrolyte analysis device. The control device performs water quality determination processing of determining whether a water quality of the diluent is normal or abnormal based on a measurement result of the water quality measurement unit.

Advantageous Effects of Invention

It is possible to suppress a burden with respect to measurement while suppressing a decrease in accuracy of the measurement result.

DESCRIPTION OF EMBODIMENTS

Hereinafter, embodiments of the invention will be described with reference to the drawings.

First Embodiment

A first embodiment of the invention will be described in detail with reference to FIGS. 1 to 3.

Figure 1:
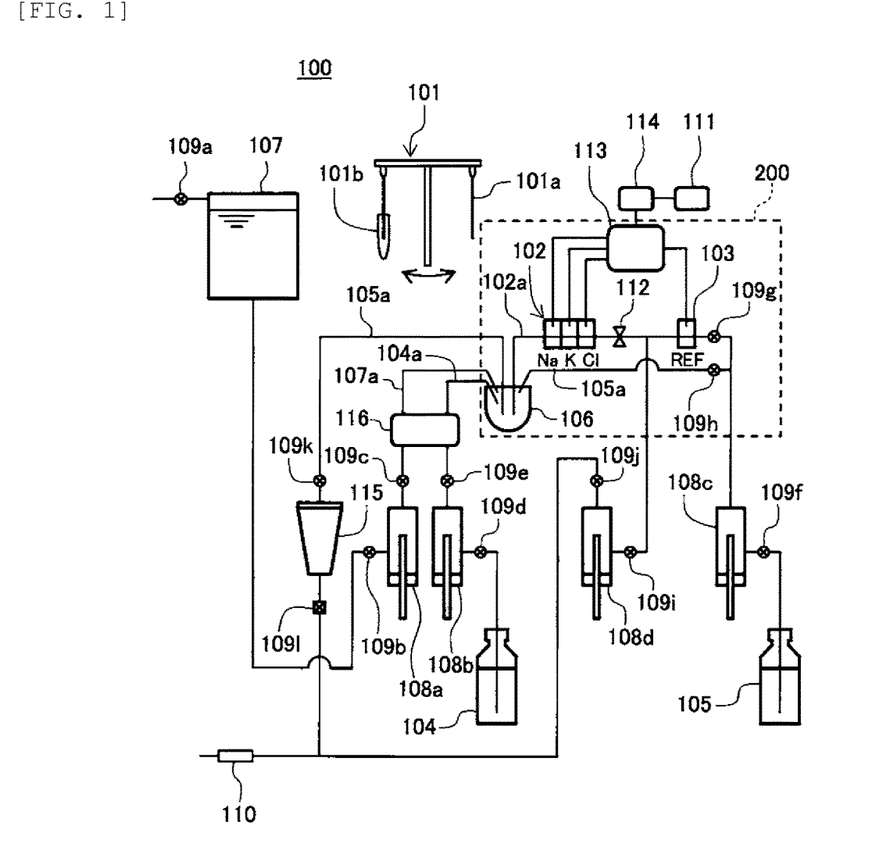
FIG. 1 is a diagram schematically showing an entire configuration an electrolyte analysis device according to a first embodiment.

FIG. 1 is a diagram schematically showing an entire configuration of an electrolyte analysis device according to the embodiment of the invention. In the present embodiment, a flow-type electrolyte analysis device (hereinafter, simply referred to as an electrolyte analysis device) using an ion selective electrode (ISE) will be described as an example of the electrolyte analysis device.

In FIG. 1, an electrolyte analysis device 100 schematically includes a specimen dispensing device 101, an ion selective electrode group 102, a reference electrode 103, a standard solution bottle 104, a reference electrode solution bottle 105, a dilution tank 106, a water supply tank 107, syringes 108a to 108d, valves 109a to 109j, a waste solution tank 110, and a control device 111.

The specimen dispensing device 101 includes a sample probe 101a and a sample vessel 101b. The sample probe 101a performs dispensing processing of aspirating a sample (such as a specimen of a patient) contained in the sample vessel 101b and discharging the sample into the dilution tank 106. Here, the specimen is a generic term for analysis targets collected from a living body of a patient, and is, for example, blood, urine, or the like. In addition, the specimen may be a specimen obtained by performing a pretreatment on the analysis targets.

The water supply tank 107 stores highly pure water (hereinafter, referred to as system water) generally used in the electrolyte analysis device. The system water is supplied to the water supply tank 107 from a pure water production device (not shown) or the like via the valve 109a. The system water stored in the water supply tank 107 is discharged into the dilution tank 106 via a system water nozzle 107a by operations of the syringe (system water syringe) 108a and the valves 109b and 109c.

The standard solution bottle 104 contains, for ion species to be measured by the electrolyte analysis device 100, a standard solution having a predetermined known ion concentration. The standard solution contained in the standard solution bottle 104 is generated so as to contain, for example, sodium ions (Na+), potassium ions (K+), and chloride ions (Cl−). The standard solution contained in the standard solution bottle 104 is discharged into the dilution tank 106 via a standard solution nozzle 104a by operations of the syringe (standard solution syringe) 108b and the valves 109d and 109e.

A temperature controller 116 is provided in a flow path of the system water nozzle 107a and the standard solution nozzle 104a, and temperatures of the system water and the standard solution passing through the flow path are adjusted to be within a predetermined constant temperature range.

The reference electrode solution bottle 105 contains a reference electrode solution having a predetermined known ion concentration. The reference electrode solution contained in the reference electrode solution bottle 105 is, for example, an aqueous solution of potassium chloride (KCl) containing potassium ions (K+). The reference electrode solution contained in the reference electrode solution bottle 105 is sent to the reference electrode 103 by operations of the syringe (reference electrode solution syringe) 108c and the valves 109f, 109g, and 109h. In addition, in water quality determination processing to be described later, the reference electrode solution contained in the reference electrode solution bottle 105 is discharged into the dilution tank 106 via a reference electrode solution nozzle 105a by the operations of the reference electrode solution syringe 108c and the valves 109f, 109g, and 109h.

The sample dispensed into the dilution tank 106 is diluted by the system water discharged from the water supply tank 107 into the dilution tank 106 via the system water nozzle 107a by the operations of the syringe (system water syringe) 108a and the valves 109b 109c, and is stirred. The present embodiment exemplifies a case where the system water is used as a diluent for diluting the sample. Alternatively, the sample may be diluted using another diluent. The sample diluted with the system water in the dilution tank 106 is sent to the ion selective electrode group 102 via a sipper nozzle 102a by operations of the syringe (sipper syringe) 108d and the valves 109i and 109j. At this time, a pinch valve 112 provided in a flow path between the ion selective electrode group 102 and the reference electrode 103 is temporarily in an ON state.

In addition, similar to the diluted sample, the standard solution discharged into the dilution tank 106 is also sent to the ion selective electrode group 102 via the sipper nozzle 102a by the operations of the syringe (sipper syringe) 108d and the valves 109l and 109j.

A plurality of ion selective electrodes constituting the ion selective electrode group 102 are each attached with an ion sensitive film having a property of changing an electromotive force according to a concentration of a specific ion (for example, sodium ion (Na+), potassium ion (K+), or chloride ion (Cl−)) in a sample solution. Accordingly, the ion selective electrode group 102 outputs the electromotive force according to the ion concentration in the sample solution.

When the pinch valve 112 is ON in a state where the diluted sample is sent to the ion selective electrode group 102 and the reference electrode solution is sent to the reference electrode 103, the diluted sample and the reference electrode solution sent in the flow path are brought into contact with each other, and the ion selective electrode group 102 and the reference electrode 103 are electrically connected to each other in the flow path.

A potential difference between each ion selective electrode of the ion selective electrode group 102 and the reference electrode 103 is measured by a voltmeter 113, and a measurement result (electric signal) is sent to the control device 111 via an amplifier 114. In addition, before or after the measurement on the diluted sample, measurement on the standard solution is performed in the same manner as the measurement on the diluted sample.

Although not shown, the control device 111 controls an entire operation of the electrolyte analysis device 100, and can be a computer including a calculation device such as a central processing unit (CPU), a storage device such as a random access memory (RAM) or a hard disk drive (HHD), and an input and output device such as an I/O port. The storage device and the input and output device can exchange data with the calculation device via an internal bus or the like. The input and output device is connected to mechanisms of the electrolyte analysis device 100, and the control device 111 controls operations of the mechanisms via the input and output device.

The control device 111 calculates a concentration of a specific electrolyte contained in the sample based on the potential difference between each ion selective electrode of the ion selective electrode group 102 and the reference electrode 103. In addition, by performing calibration based on a measurement result of the standard solution, an electrolyte concentration in the sample can be measured more accurately. A specific calibration method can be appropriately designed by those skilled in the art based on a known technique or the like. The control device 111 stores in a storage unit (not shown) the ion concentration calculated for each ion and outputs the ion concentration to an output device (for example, a display device).

The sample and the standard solution remaining in the dilution tank 106 are aspirated by a waste solution nozzle 115a by operations of a vacuum bottle 115 and valves 109k and 109l, and are sent to the waste solution tank 110.

In the electrolyte analysis device 100 according to the present embodiment configured as described above, the ion concentration of the system water in the water supply tank 107 is measured by a water quality measurement unit 200 (the ion selective electrode group 102, the reference electrode 103, and the voltmeter 113), and the control device 111 performs the water quality determination processing of determining whether a water quality of the system water is normal or abnormal based on a measurement result.

First, a principle of the water quality determination processing according to the present embodiment will be described.

Figure 2:
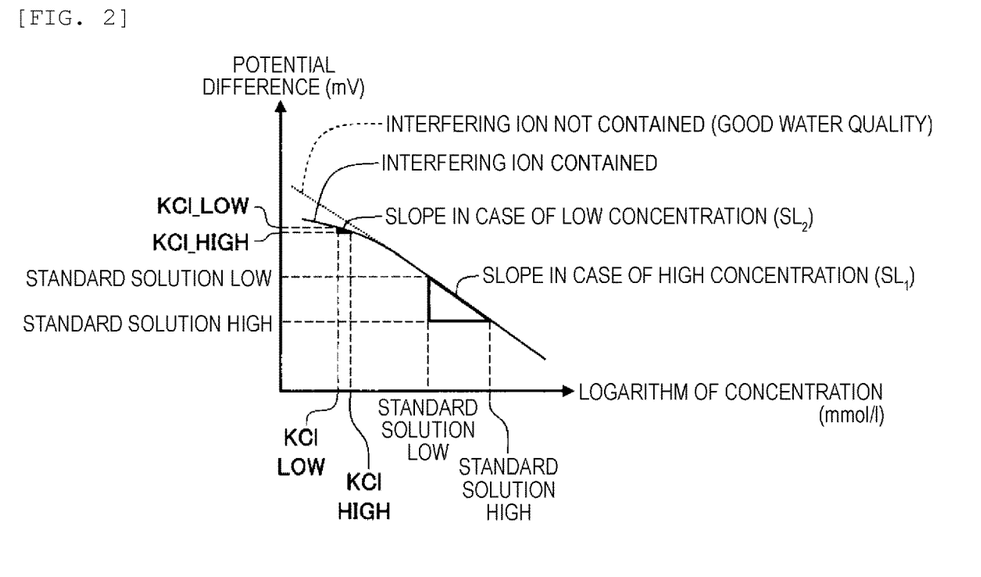
FIG. 2 is a diagram showing a relationship between a potential difference between a system water ion selective electrode in which potassium chloride is dissolved and a reference electrode, and a concentration of potassium chloride when system water in which potassium chloride is dissolved is measured by the electrolyte analysis device.

FIG. 2 is a diagram showing a relationship between the potential difference between a system water (hereinafter, referred to as a potassium chloride solution) ion selective electrode in which potassium chloride (KCl) is dissolved and a reference electrode, and the concentration of potassium chloride when system water in which potassium chloride (KCl) is dissolved is measured by the electrolyte analysis device.

As shown in FIG. 2, for example, when the potassium chloride solution does not contain ions that interfere ion selectivity of the ion selective electrode group 102 (hereinafter referred to as interfering ions), a logarithm of concentration (mmol/l) and the potential difference (mV) show a proportional relationship regardless of whether the concentration of potassium chloride is high or low. On the other hand, when the potassium chloride solution contains a certain amount or more of interfering ions, and when the concentration of potassium chloride is low, the relationship between the logarithm of concentration (mmol/l) and the potential difference (mV) deviates from the proportional relationship, and a slope of the relationship between the logarithm of concentration (mmol/l) and the potential difference (mV) changes. A change in slope is more significant as the interfering ion concentration is higher. When the concentration of potassium chloride is high, the slope of the relationship between the logarithm of degree (mmol/l) and the potential difference (mV) does not substantially change regardless of presence or absence of the interfering ions (when the interfering ion concentration is sufficiently lower than the concentration of potassium chloride).

Therefore, the interfering ion concentration in the system water is estimated by generating, using the system water, a plurality of types of potassium chloride solutions having different known concentrations including a high concentration and a low concentration, measuring the potential difference between the ion selective electrode group 102 and the reference electrode 103, and obtaining the slope of the relationship between the logarithm of degree (mmol/l) and the potential difference (mV). In addition, by experimentally obtaining the slope of the relationship between the logarithm of concentration (mmol/l) and the potential difference (mV) while changing the interfering ion concentration with respect to the system water, it is possible to obtain a slope at a boundary between the interfering ion concentration at which an influence on a measurement accuracy of the electrolyte analysis device 100 is allowable and the interfering ion concentration at which the influence is not allowable. Therefore, by using the slope as a threshold, it is possible to perform the water quality determination processing of determining whether the water quality of the system water is good (normal) or abnormal.

In the present embodiment, the water quality determination processing is performed based on a result of measuring a plurality of types (for example, two types) of diluted standard solutions having different known concentrations, which are prepared by diluting the standard solution with the system water, and a plurality of types (for example, two types) of diluted reference electrode solutions having different known concentrations, which are prepared by diluting the reference electrode solution with the system water.

Specifically, the standard solution in the standard solution bottle 104 is discharged into the dilution tank 106 via the standard solution nozzle 104a, and the system water in the water supply tank 107 is discharged into the dilution tank 106 via the system water nozzle 107a, thereby diluting the standard solution having a known concentration with the system water at a predetermined ratio to generate diluted standard solutions. The concentration of the diluted standard solution includes, for example, two types of concentrations of chloride ion (Cl−), i.e., 80 (mmol/l) and 120 (mmol/l). The potential difference between the ion selective electrode group 102 and the reference electrode 103 is measured by the voltmeter 113 for each of the diluted standard solutions having two concentrations, and measurement results are plotted with a horizontal axis representing the electrolyte concentration (logarithm) and a vertical axis representing the potential difference. Then, a linear regression line is drawn between two points of the measurement results, and a slope thereof is calculated. The slope is defined as a slope (SL1) in a case of a high concentration.

In addition, the reference electrode solution in the reference electrode solution bottle 105 is discharged into the dilution tank 106 via the reference electrode solution nozzle 105a, and the system water in the water supply tank 107 is discharged into the dilution tank 106 via the system water nozzle 107a, thereby diluting the reference electrode solution having a known concentration with the system water at predetermined ratio to generate diluted reference electrode solutions. The concentration of the diluted reference electrode solution is lower than that of the diluted standard solution. That is, the concentration of the diluted reference electrode solution includes, for example, two types of concentrations of chloride ion (Cl−), i.e., 8 (mmol/l) and 12 (mmol/1). The potential difference between the ion selective electrode group 102 and the reference electrode 103 is measured by the voltmeter 113 for each of the diluted reference electrode solutions having two concentrations, and measurement results are plotted with the horizontal axis representing the electrolyte concentration (logarithm) and the vertical axis representing the potential difference. Then, a linear regression line is drawn between two points of the measurement results, and a slope thereof is calculated. The slope is defined as a slope (SL2) in a case of a low concentration.

For example, when a measurement lower limit value of each ion selective electrode of the ion selective electrode group 102 is sufficiently lower than 0.2 (mmol/l), and when the system water does not contain the interfering ions, the slope SL1 calculated for the diluted standard solutions and the slope SL2 calculated for the diluted reference electrode solutions show the same value. Therefore, a ratio of the slope SL2 to the slope SL1 is (SL2/SL1×100)=100 (%). On the other hand, when the system water contains the interfering ions, measurement sensitivity in a low concentration region decreases due to the influence of the interfering ions, and therefore, the ratio (SL2/SL1×100) of the slope SL2 to the slope SL1 as a reference is lower than 100 (%). For example, assuming that a threshold of the interfering ion concentration set in consideration of the influence of the interfering ions on the measurement accuracy is 1.0 (mmol/l), when the ratio (SL2/SL1×100) of the slope SL2 to the slope SL1 is 92 (%) or less, it can be determined that the influence on the measurement accuracy is not allowable, that is, the water quality of the system water is abnormal.

The slope sensitivities SL1 and SL2 can be calculated according to the following (equation 1) and (equation 2), respectively.

$$SL1 = (EMFH - EMFL)/(\text{Log } CH - \text{Log } CL) \quad \text{(Equation 1)}$$

Here, EMFH is a measured electromotive force of the diluted standard solution at a high concentration, EMFL is a measured electromotive force of the diluted standard solution at a low concentration, CH is a specified concentration value of the diluted standard solution at a high concentration, and CL is a specified concentration value of the diluted standard solution at a low concentration.

$$SL2 = (EMFH - EMFL)/(\text{Log } CH - \text{Log } CL) \quad \text{(Equation 1)}$$

Here, EMFH is a measured electromotive force of the diluted standard solution at a high concentration, EMFL is a measured electromotive force of the diluted standard solution at a low concentration, CH is a specified concentration value of the diluted standard solution at a high concentration, and CL is a specified concentration value of the diluted standard solution at a low concentration.

In addition, a concentration of an internal standard solution concentration is calculated according to the following (equation 2) and (equation 3).

$$CIS = CL \times 10a \quad \text{(Equation 2)}$$

$$a = (EMFIS - EMFL)/SL \quad \text{(Equation 3)}$$

Here, CIS is the internal standard solution concentration, and EMFIS is an electromotive force of an internal standard solution.

In addition, a concentration of the sample is calculated according to the following (equation 4).

$$E = E0 + (2.303RT/zF) \cdot \log CS \quad \text{(Equation 4)}$$

Here, CS is the concentration of the sample, E is a potential difference (mV) generated between the ion selective electrode and the reference electrode, E0 is a reference potential (mV), R is a gas constant (8.3144 J·mol−1·K−1), T is an absolute temperature (273.15+° C.), n is an ion valence, and F is a Faraday constant (96.485 C·mol).

Figure 3:
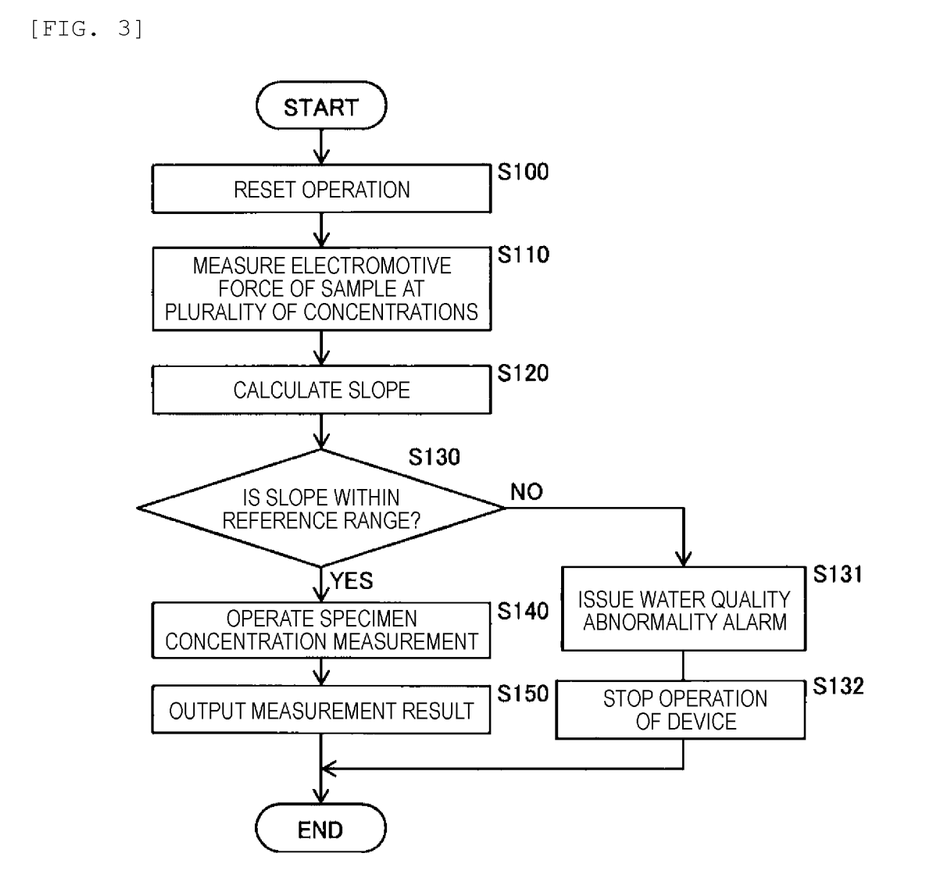
FIG. 3 is a flowchart illustrating water quality determination processing according to the first embodiment.

FIG. 3 is a flowchart illustrating the water quality determination processing.

In FIG. 3, when an analysis start is instructed, the control device 111 first performs a reset operation (step S100).

Subsequently, diluted standard solutions and diluted reference electrode solutions each having a plurality of concentrations are generated and measured by the water quality measurement unit 200 (the ion selective electrode group 102, the reference electrode 103, and the voltmeter 113), and electromotive forces (potential differences) of the solutions are measured (step S110).

Subsequently, the slopes SL1 and SL2 are calculated based on the diluted standard solutions and the diluted reference electrode solutions (step S120), and it is determined whether the slope SL2 is within a reference range (step S130). Here, whether the slope SL2 is within the reference range is, for example, whether the ratio (SL2/SL1×100) of the slope SL2 to the slope SL1 is 92 (%) or more as described above.

When a determination result in step S130 is YES, it is determined that the water quality of the system water is normal (good), a specimen concentration measurement operation is performed (step S140), a measurement result is output (step S150), and the processing ends. At this time, since the water quality of the system water is ensured, the measurement result can be obtained with high accuracy.

When the determination result in step S130 is NO, it is determined that the water quality of the system water is abnormal, a water quality abnormality alarm is issued (step S131), the operation of the device is stopped (step S132), and the processing ends. At this time, since it is detected that the water quality of the system water is abnormal and the measurement of the specimen is not performed, measurement with low accuracy (low reliability) can be prevented from being performed, and an operator can be notified the abnormality and be prompted to rapidly improve and eliminate the abnormal state.

Effects of the present embodiment configured as described above will be described.

In the related art in which a silver nitrate solution (AgNO3) is used as a diluent, a wastewater treatment is indispensable in consideration of environmental load, and the wastewater treatment causes an increase in treatment cost and treatment time. In particular, in large-scale hospitals or clinical test centers that perform a large number of measurement treatments, a usage of the diluent and the amount of wastewater are large. Therefore, a burden such as running cost is enormous. In the related art in which a diluent is generated by mixing a stock solution of the diluent and pure water, since the pure water is not standardized, there is a possibility that an error occurs in a measurement result of an electrolyte analysis device due to an unspecified ion contained in the pure water.

In contrast, in the present embodiment, the electrolyte analysis device 100 that measures a concentration of a specific ion in a sample using a plurality of ion selective electrodes of the ion selective electrode group 102 and the reference electrode 103 includes: the water supply tank 107 that stores system water used for at least one of solution sending, probe cleaning, and temperature adjustment in the electrolyte analysis device 100; the specimen dispensing device 101 that dispenses a sample to be measured; the dilution tank 106 that dilutes the sample dispensed by the specimen dispensing device 101 with the system water; the water quality measurement unit 200 that measures an ion concentration of the system water in the water supply tank 107; and the control device 111 that controls the electrolyte analysis device 100. Since the control device 111 performs water quality determination processing of determining whether the water quality of the system water is normal or abnormal based on a measurement result of the water quality measurement unit 200, a burden with respect to measurement can be suppressed while suppressing a decrease in accuracy of the measurement result.

Second Embodiment

A second embodiment of the invention will be described with reference to FIGS. 4 to 6.

The present embodiment exemplifies a case where a spectrophotometer 117 is provided as a water quality measurement unit 200A of an electrolyte analysis device 100A.

Figure 4:
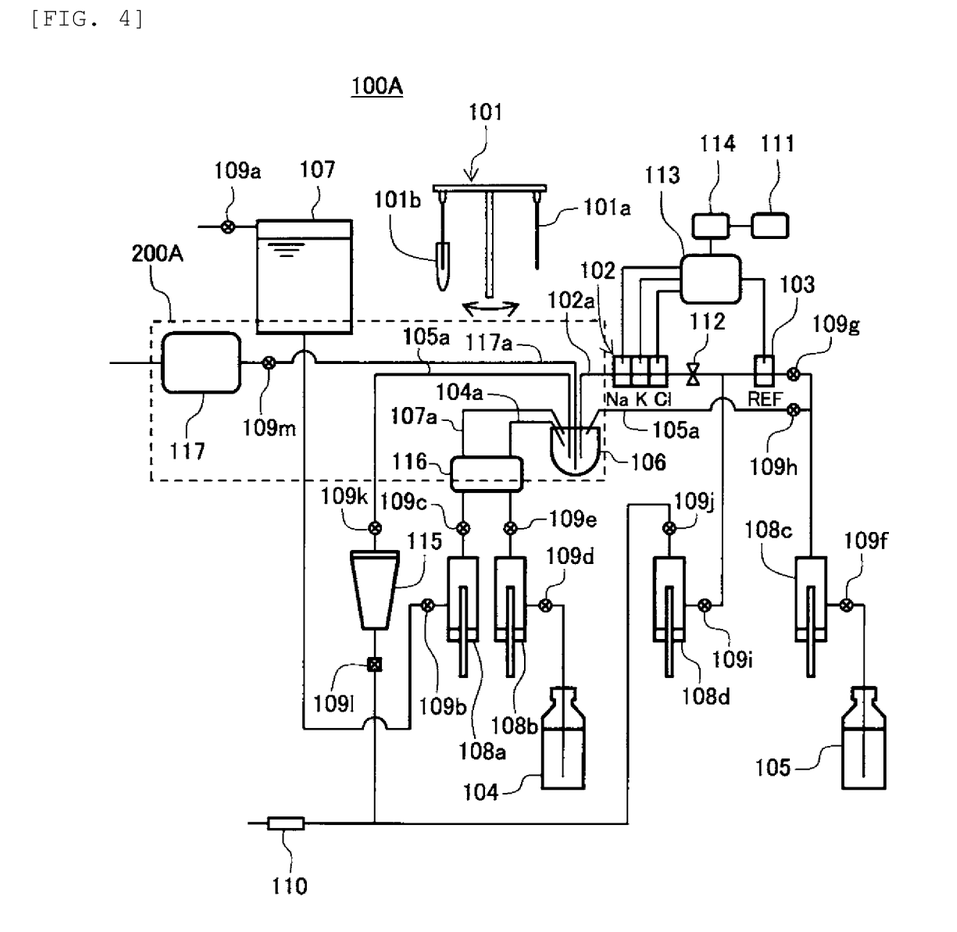
FIG. 4 is a diagram schematically showing an entire configuration of an electrolyte analysis device according to a second embodiment.

FIG. 4 is a diagram schematically showing an entire configuration of an electrolyte analysis device according to the embodiment of the invention. In the drawing, the same members as those in the first embodiment are denoted by the same reference numerals, and the description thereof will be omitted.

In FIG. 4, the electrolyte analysis device 100A schematically includes the specimen dispensing device 101, the ion selective electrode group 102, the reference electrode 103, the standard solution bottle 104, the reference electrode solution bottle 105, the dilution tank 106, the water supply tank 107, the syringes 108a to 108d, the valves 109a to 109j, the waste solution tank 110, and the control device 111.

In addition, the electrolyte device 100A includes, as the water quality measurement unit 200A, the spectrophotometer 117 that measures absorbance or luminescence intensity of system water to which a predetermined reagent is added. The spectrophotometer 117 includes a reagent bottle (not shown) for containing a photometric reagent, and the photometric reagent is discharged into the dilution tank 106 via a spectrophotometer nozzle 117a by operations of a valve 109m and a syringe (not shown). In addition, by the operations of the valve 109m and the syringe (not shown), the system water with a photometric reagent added thereto in the dilution tank 106 is sent to the spectrophotometer 117 via the spectrophotometer nozzle 117a. The control device 111 performs water quality determination processing based on a measurement result of the spectrophotometer 117.

In the electrolyte analysis device 100A according to the present embodiment configured as described above, an ion concentration of the system water in the water supply tank 107 is measured by the water quality measurement unit 200A (the spectrophotometer 117), and the control device 111 performs the water quality determination processing of determining whether the water quality of the system water is normal or abnormal based on a measurement result.

First, a principle of the water quality determination processing according to the present embodiment will be described.

Figure 5:
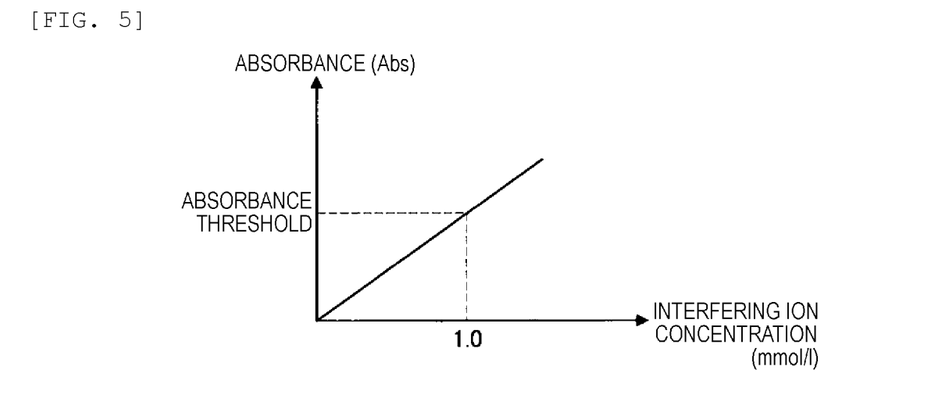
FIG. 5 is a diagram showing a relationship between an interfering ion concentration and absorbance when system water with a photometric reagent added thereto is measured.

FIG. 5 is a diagram showing a relationship between an interfering ion concentration and the absorbance when the system water with a photometric reagent added thereto is measured.

As the photometric reagent, for example, a reagent using an enzyme that consumes sodium ions (Na+) to decompose a substrate is used in absorbance measurement. In addition, for example, a reagent using a molecule which is referred to as an optode and which emits fluorescence by being bonded to a specific ion considered to be an interfering ion is used in luminescence intensity measurement.

As shown in FIG. 5, in absorbance measurement, the relationship between the interfering ion concentration (mmol/l) in the system water and the absorbance (Abs) shows a proportional relationship in which the absorbance increases as the interfering ion concentration increases.

Therefore, the interfering ion concentration in the system water is estimated by measuring the absorbance of the system water with a photometric reagent added thereto.

For example, when a threshold of the interfering ion concentration set in consideration of the influence of the interfering ions on measurement accuracy is set to 1.0 (mmol/l) and an absorbance threshold corresponding to the threshold of the interfering ion concentration is set, and when the absorbance is equal to or higher than the absorbance threshold, it can be determined that the influence on the measurement accuracy is not allowable, that is, the water quality of the system water is abnormal. In this way, it is possible to perform the water quality determination processing of determining whether the water quality of the system water is good (normal) or abnormal.

The water quality determination processing can also be performed in the same manner when the luminescence intensity of the system water with a photometric reagent added thereto is measured. That is, since in luminescence intensity measurement, the relationship between the interfering ion concentration in the system water and the luminescence intensity shows a proportional relationship in which the luminescence intensity increases as the interfering ion concentration increases, when the luminescence intensity is equal to or higher than a predetermined threshold of the luminescence (for example, based on the interfering ion concentration of 1.0 mmol/l), it can be determined that the water quality of the system water is abnormal.

Figure 6:
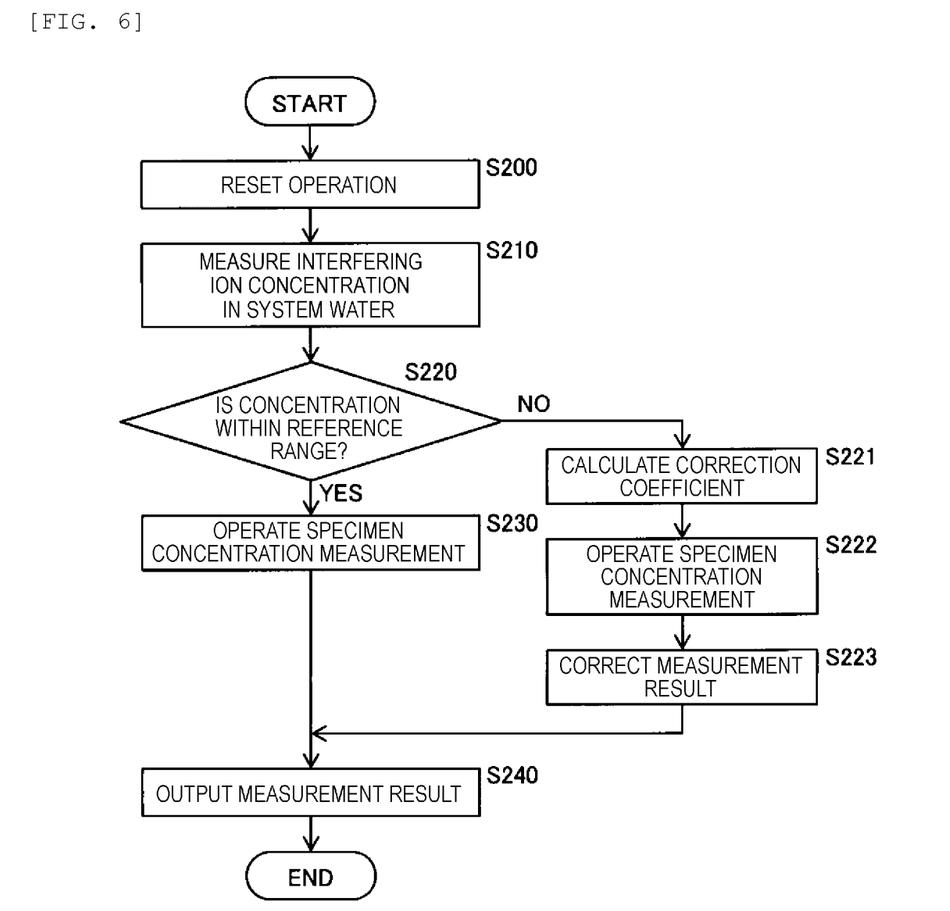
FIG. 6 is a flowchart illustrating water quality determination processing according to the second embodiment.

FIG. 6 is a flowchart illustrating the water quality determination processing according to the present embodiment.

In FIG. 6, when an analysis start is instructed, the control device 111 first performs a reset operation (step S200).

Subsequently, a photometric reagent is added to the system water in the dilution tank 106, measurement by the water quality measurement unit 200A (the spectrophotometer 117) is performed, and the interfering ion concentration is calculated based on the absorbance (step S210).

Subsequently, it is determined whether the interfering ion concentration is within a reference range, that is, whether the absorbance is equal to or less than the absorbance threshold, and when a determination result is YES, it is determined that the water quality of the system water is normal (good), a specimen concentration measurement operation is performed (step S230), a measurement result is output (step S240), and the processing ends. At this time, since the water quality of the system water is ensured, the measurement result can be obtained with high accuracy.

When the determination result in step S220 is NO, it is determined that the water quality of the system water is abnormal, a correction coefficient is calculated (step S221), a specimen measurement operation is performed (step S222), correction is performed by applying the correction coefficient to a measurement result (step S223), and the processing ends.

Here, the correction coefficient is for correcting fluctuation of a specimen measurement result caused by the influence of the interfering ions, and for example, by experimentally calculating a fluctuation amount of the specimen measurement result with respect to the interfering ion concentration in advance and applying the correction coefficient according to the measured interfering ion concentration to the specimen measurement result, it is possible to obtain a measurement result with higher accuracy. That is, even when it is detected that the water quality of the system water is abnormal, since the specimen measurement result is corrected according to the interfering ion concentration, it is possible to perform measurement with high accuracy without stopping the specimen measurement operation.

Other configurations are the same as those of the first embodiment.

In the present embodiment configured as described above, the same effects as those of the first embodiment can also be obtained.

Third Embodiment

A third embodiment of the invention will be described with reference to FIGS. 7 and 8.

The present embodiment exemplifies a case where an electric conductivity measurement device 118 is provided as a water quality measurement unit 200B of an electrolyte analysis device 100B.

Figure 7:
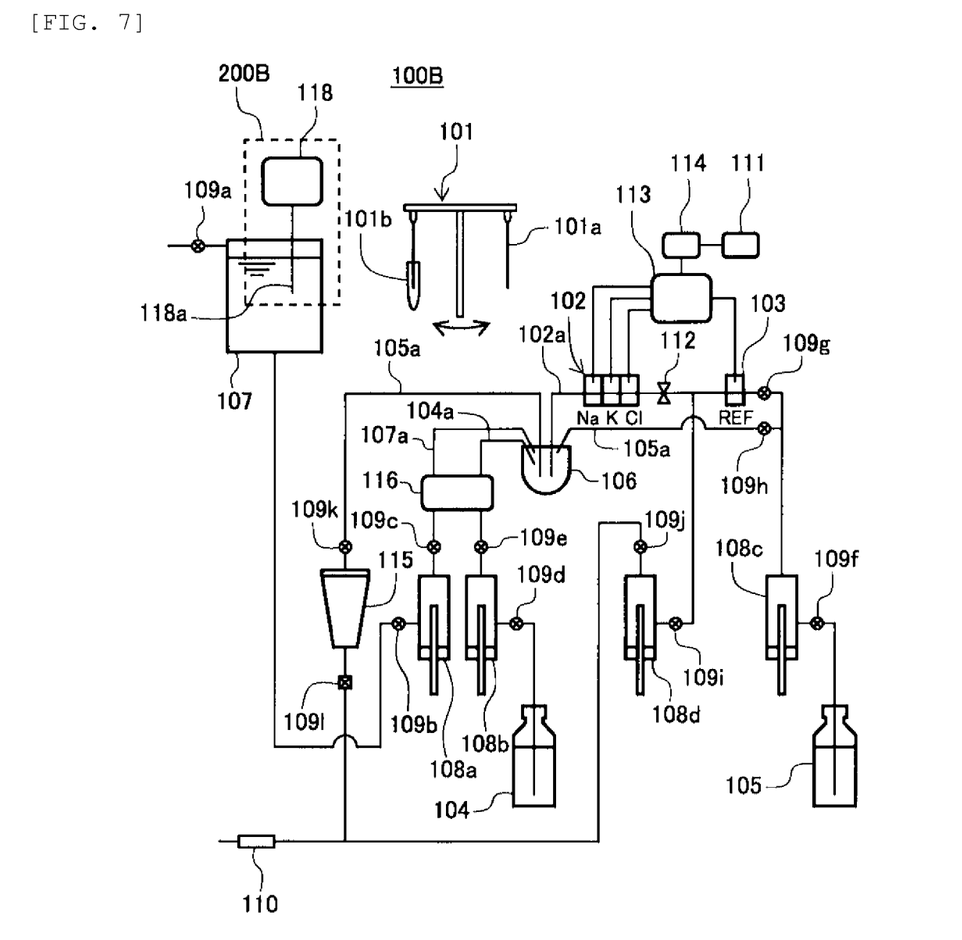
FIG. 7 is a diagram schematically showing an configuration of an electrolyte analysis device entire according to a third embodiment.

FIG. 7 is a diagram schematically showing an entire configuration of an electrolyte analysis device according to the embodiment of the invention. In the drawing, the same members as those in the first embodiment are denoted by the same reference numerals, and the description thereof will be omitted.

In FIG. 7, the electrolyte analysis device 100B schematically includes the specimen dispensing device 101, the ion selective electrode group 102, the reference electrode 103, the standard solution bottle 104, the reference electrode solution bottle 105, the dilution tank 106, the water supply tank 107, the syringes 108a to 108d, the valves 109a to 109j, the waste solution tank 110, and the control device 111.

In addition, the electrolyte analysis device 100B includes, as the water quality measurement unit 200B, the electric conductivity measurement device 118 that measures an electric conductivity of system water stored in the water supply tank 107. The electric conductivity measurement device 118 includes an electric conductivity measurement terminal 118a inserted into the water supply tank 107, and measures the electric conductivity of the system water stored in the water supply tank 107. The control device 111 performs water quality determination processing based on a measurement result of the electric conductivity measurement device 118.

In the electrolyte analysis device 100B according to the present embodiment configured as described above, the electric conductivity of the system water in the water supply tank 107 is measured by the water quality measurement unit 200B (the electric conductivity measurement device 118), and the control device 111 performs the water quality determination processing of determining whether the water quality of the system water is normal or abnormal based on a measurement result.

First, a principle of the water quality determination processing according to the present embodiment will be described.

Figure 8:
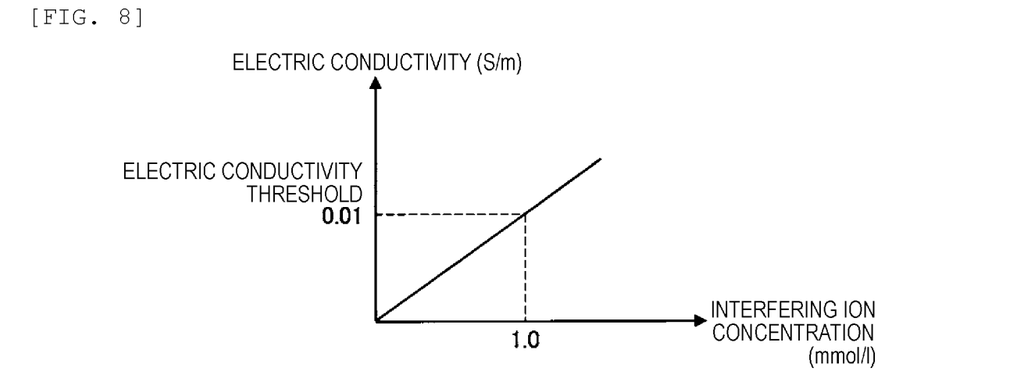
FIG. 8 is a diagram showing a relationship between an interfering ion concentration and an electric conductivity when an electric conductivity of system water is measured.

FIG. 8 is a diagram showing a relationship between an interfering ion concentration in the system water and the electric conductivity when the electric conductivity is measured.

As shown in FIG. 8, the relationship between the interfering ion concentration (mmol/l) in the system water and the electric conductivity (S/m) shows a proportional relationship in which the electric conductivity increases as the interfering ion concentration increases.

Therefore, the interfering ion concentration in the system water is estimated by measuring the electric conductivity of the system water.

For example, when a threshold of the interfering ion concentration set in consideration of the influence of the interfering ions on a measurement accuracy is set to 1.0 (mmol/l) and the electric conductivity (for example, 0.01 S/m) corresponding to the threshold of the interfering ion concentration is set as an electric conductivity threshold, and when the electric conductivity is equal to or higher than the electric conductivity threshold, it can be determined that the influence on the measurement accuracy is not allowable, that is, the water quality of the system water is abnormal. Thus, it is possible to perform the water quality determination processing of determining whether the water quality of the system water is good (normal) or abnormal.

Other configurations are the same as those of the first embodiment.

In the present embodiment configured as described above, the same effects as those of the first embodiment can also be obtained.

Other Embodiments

The invention is not limited to the above embodiments, and includes various modifications and combinations without departing from the gist of the invention.

(1) For example, the first embodiment exemplifies a case where a water quality abnormality alarm is issued to stop the operation of the device (see steps S131 and S132 in FIG. 3) when it is determined that the water quality of the system water is abnormal. Alternatively, as in the second embodiment, when it is determined that the water quality of the system water is abnormal, a correction coefficient may be calculated and applied to a specimen measurement result (see steps S221 to S223 in FIG. 6). This also applies to the third embodiment.

(2) In addition, the second embodiment exemplifies a case where a correction coefficient is calculated and applied to a specimen measurement result (see steps S221 to S223 in FIG. 6) when it is determined that the water quality of the system water is abnormal. Alternatively, as in the first embodiment, when it is determined that the water quality of the system water is abnormal, a water quality abnormality alarm may be issued to stop the operation of the device (see steps S131 and S132 in FIG. 3).

Appendix

The invention is not limited to the above embodiments, and includes various modifications and combinations without departing from the gist of the invention. In addition, the invention is not limited to the configuration including all the configurations described in the above embodiments, and includes a configuration in which a part of the configuration is deleted. In addition, each of the above configurations, functions, and the like may be implemented by designing a part or all of the configurations, functions, and the like in, for example, an integrated circuit. In addition, each of the above configurations, functions, and the like may be implemented by software by a processor interpreting and executing a program for implementing each function.

REFERENCE SIGNS LIST 100, 100A, 100B: electrolyte analysis device
101: specimen dispensing device
101a: sample probe
101b: sample vessel
102: ion selective electrode group
102a: sipper nozzle
103: reference electrode
104: standard solution bottle
104a: standard solution nozzle
105: reference electrode solution bottle
105a: reference electrode solution nozzle
106: dilution tank
107: water supply tank
107a: system water nozzle
108a: system water syringe
108b: standard solution syringe
108c: reference electrode solution syringe
108d: sipper syringe
109a to 109m: valve
110: waste solution tank
111: control device
112: pinch valve
113: voltmeter
114: amplifier
115: vacuum bottle
115a: waste solution nozzle
116: temperature controller
117: spectrophotometer
117a: spectrophotometer nozzle
118: electric conductivity measurement device
118a: electric conductivity measurement terminal
200, 200A, 200B: water quality measurement unit

The invention claimed is:

1. An electrolyte analysis device that measures a concentration of a specific ion in a sample using a plurality of ion selective electrodes and a reference electrode, the electrolyte analysis device comprising:
    a water supply tank configured to store a diluent used for at least one of solution sending, probe cleaning, and temperature adjustment in the electrolyte analysis device;
    a specimen dispensing device configured to dispense a sample to be measured;
    a dilution tank configured to dilute the sample dispensed by the specimen dispensing device with the diluent;
    a water quality measurement unit configured to measure an ion concentration of the diluent in the water supply tank, which is an electrolyte analysis unit including the plurality of ion selective electrodes and the reference electrode; and
    a control device configured to control the electrolyte analysis device, wherein
    in the measurement of the specific ion in the sample, the control device is configured to dilute a reference electrode solution in contact with measuring the reference electrode to a plurality of concentrations with the diluent, and perform water quality determination processing to determine whether a water quality of the diluent is normal or abnormal based on a slope at a lower concentration of the reference electrode solution than a standard solution, which are determined from measurement results.

2. The electrolyte analysis device according to claim 1, further comprising:
    a reference electrode solution nozzle configured to discharge the reference electrode solution into the dilution tank.

3. The electrolyte analysis device according to claim 1, wherein
    the plurality of ion selective electrodes of the water quality measurement unit include an ion selective electrode configured to selectively detect potassium ions or chloride ions, and
    the reference electrode solution contains potassium chloride.

4. The electrolyte analysis device according to claim 1, wherein
    in the water quality determination processing, the control device corrects the measurement result of the sample using a correction coefficient predetermined according to the ion concentration of the diluent when it is determined that the water quality of the diluent is abnormal.

5. The electrolyte analysis device according to claim 1, wherein
    in the water quality determination processing, an alarm is issued when it is determined that the water quality of the diluent is abnormal.

6. The electrolyte analysis device according to claim 1, wherein
    the diluent is system water.

7. The electrolyte analysis device according to claim 1, wherein the control device is configured to dilute a standard solution in contact with the ion selective electrode to a plurality of concentrations with the diluent, and plot the measurement results from the electrolyte analysis unit, with a horizontal axis representing a logarithm of an electrolyte concentration and a vertical axis representing a potential difference between an ion selective electrode group and the reference electrode.

8. The electrolyte analysis device according to claim 1, wherein the control device is configured to determine whether the water quality of the diluent is normal or abnormal based on a ratio of the slope at the lower concentration of the reference electrode solution.

* * * * *